United States Patent
Kimura et al.

(10) Patent No.: US 10,578,603 B2
(45) Date of Patent: Mar. 3, 2020

(54) BLOOD ANALYZER, BLOOD ANALYZING METHOD, AND NON-TRANSITORY STORAGE MEDIUM

(71) Applicant: Sysmex Corporation, Kobe-shi, Hyogo (JP)

(72) Inventors: Konobu Kimura, Kobe (JP); Kinya Uchihashi, Kobe (JP); Jo Linssen, Norderstedt (DE); Jarob Saker, Norderstedt (DE)

(73) Assignee: Sysmex Corporation, Kobe (JP)

( * ) Notice: Subject to any disclaimer, the term of this patent is extended or adjusted under 35 U.S.C. 154(b) by 148 days.

(21) Appl. No.: 14/740,815

(22) Filed: Jun. 16, 2015

(65) Prior Publication Data

US 2015/0369793 A1  Dec. 24, 2015

(30) Foreign Application Priority Data

Jun. 19, 2014 (JP) .................. 2014-126606

(51) Int. Cl.
| | |
|---|---|
| *G01N 33/49* | (2006.01) |
| *G01N 15/14* | (2006.01) |
| *G01N 21/64* | (2006.01) |
| *G01N 15/00* | (2006.01) |
| *G01N 21/51* | (2006.01) |
| *G01N 15/10* | (2006.01) |

(52) U.S. Cl.
CPC ......... *G01N 33/49* (2013.01); *G01N 15/1429* (2013.01); *G01N 15/1459* (2013.01); *G01N 21/51* (2013.01); *G01N 21/6428* (2013.01); *G01N 2015/008* (2013.01); *G01N 2015/1006* (2013.01); *G01N 2015/1402* (2013.01); *G01N 2021/6439* (2013.01)

(58) Field of Classification Search
CPC ............... G01N 33/49; G01N 15/1459; G01N 15/1429; G01N 21/6428; G01N 21/51; G01N 2015/1006; G01N 2015/008; G01N 2015/1402; G01N 2021/6439
See application file for complete search history.

(56) References Cited

U.S. PATENT DOCUMENTS

| | | | |
|---|---|---|---|
| 2005/0069959 A1 | 3/2005 | Yoshida et al. | |
| 2009/0105963 A1 | 4/2009 | Laursen et al. | |
| 2012/0115159 A1* | 5/2012 | Kono | G01N 33/56972 435/6.19 |
| 2012/0282601 A1* | 11/2012 | Abe | G01N 15/1459 435/6.1 |
| 2014/0051071 A1 | 2/2014 | Yoshida et al. | |
| 2014/0147837 A1 | 5/2014 | Kimura et al. | |

FOREIGN PATENT DOCUMENTS

| | | |
|---|---|---|
| JP | H06-207942 | 7/1994 |
| JP | 2005-106484 A | 4/2005 |
| JP | 2012-233754 A | 11/2012 |
| JP | 2012-233889 A | 11/2012 |
| WO | WO 2011/001681 A1 | 1/2011 |
| WO | WO 2012/147451 A1 | 11/2012 |

* cited by examiner

*Primary Examiner* — Taeyoon Kim
(74) *Attorney, Agent, or Firm* — Brinks Gilson & Lione

(57) ABSTRACT

A blood analyzer comprises a sample preparing part, a light source, a light receiving part, and a processing part configured to discriminate and count reactive B lymphocytes based on at least one of fluorescent light signals and forward scattered light signals.

6 Claims, 8 Drawing Sheets

BLOOD ANALYZER, BLOOD ANALYZING METHOD, AND NON-TRANSITORY STORAGE MEDIUM

CROSS REFERENCE TO RELATED APPLICATION

This application claims priority from prior Japanese Patent Application No. 2014-126606, filed on Jun. 19, 2014, entitled "BLOOD ANALYZER, BLOOD ANALYZING METHOD, AND BLOOD ANALYZING PROGRAM" the entire contents of which are incorporated herein by reference.

FIELD OF THE INVENTION

The invention relates to a blood analyzer, blood analyzing method, and blood analyzing program.

BACKGROUND

White blood cells such as lymphocytes, monocytes, basophils, eosinophils and neutrophils are present in normal peripheral blood. Abnormal white blood cells which are not present in normal peripheral blood appear in diseases such as viral infections or hematopoietic tumors. Abnormal white blood cells include, for example, reactive lymphocytes which have been activated by antigen stimulation.

For example, Japanese laid-open patent No. 2012-233754 discloses a method of classifying and counting white blood cells which is capable of discriminating blasts and atypical lymphocytes in addition to classifying and counting normal white blood cells.

Atypical lymphocytes include reactive B lymphocytes and reactive T lymphocytes. However, although the method disclosed in Patent Document 1 can discriminate atypical lymphocytes, this method cannot discriminate and count reactive B lymphocytes alone. A blood analyzer and blood analyzing method capable of discriminating and counting reactive B lymphocytes is therefore desirable.

SUMMARY OF THE INVENTION

The blood analyzer of the present invention includes a sample preparing part configured to prepare a measurement sample by mixing a blood sample, a fluorescent dye for staining nucleic acid, and a hemolytic agent to hemolyze red blood cells; a light source configured to irradiate light on the measurement sample; a light receiving part configured to receive fluorescent light, forward scattered light, and side scattered light given off by the measurement sample irradiated by light, and output fluorescent light signals corresponding to the intensity of the fluorescent light, forward scattered light signals corresponding to the intensity of the forward scattered light, and side scattered light signals corresponding to the intensity of the side scattered light; and a processing part configured to discriminate and count the reactive B lymphocytes based on at least one of the fluorescent light signal and forward scattered light signal.

The blood analyzing method of the present invention includes a step of obtaining fluorescent light signals corresponding to the intensity of the fluorescent light, forward scattered light signals corresponding to the intensity of the forward scattered light, and side scattered light signals corresponding to the intensity of side scattered light given off when the measurement sample is irradiated by light; and a step of discriminating and counting the reactive B lymphocytes based on at least one of the fluorescent light signal and forward scattered light signal.

The non-transitory storage medium of the present invention stores a computer program for causing a computer to execute obtaining fluorescent light signals corresponding to the intensity of the fluorescent light, forward scattered light signals corresponding to the intensity of the forward scattered light, and side scattered light signals corresponding to the intensity of side scattered light given off when a measurement sample is irradiated by light, and discriminating and counting the reactive B lymphocytes based on at least one of the fluorescent light signals and forward scattered light signals.

DETAILED DESCRIPTION OF THE PREFERRED EMBODIMENTS

A preferred embodiment of the present invention is described in the following examples.

Blood Analyzer 100 Structure

Figure 1:
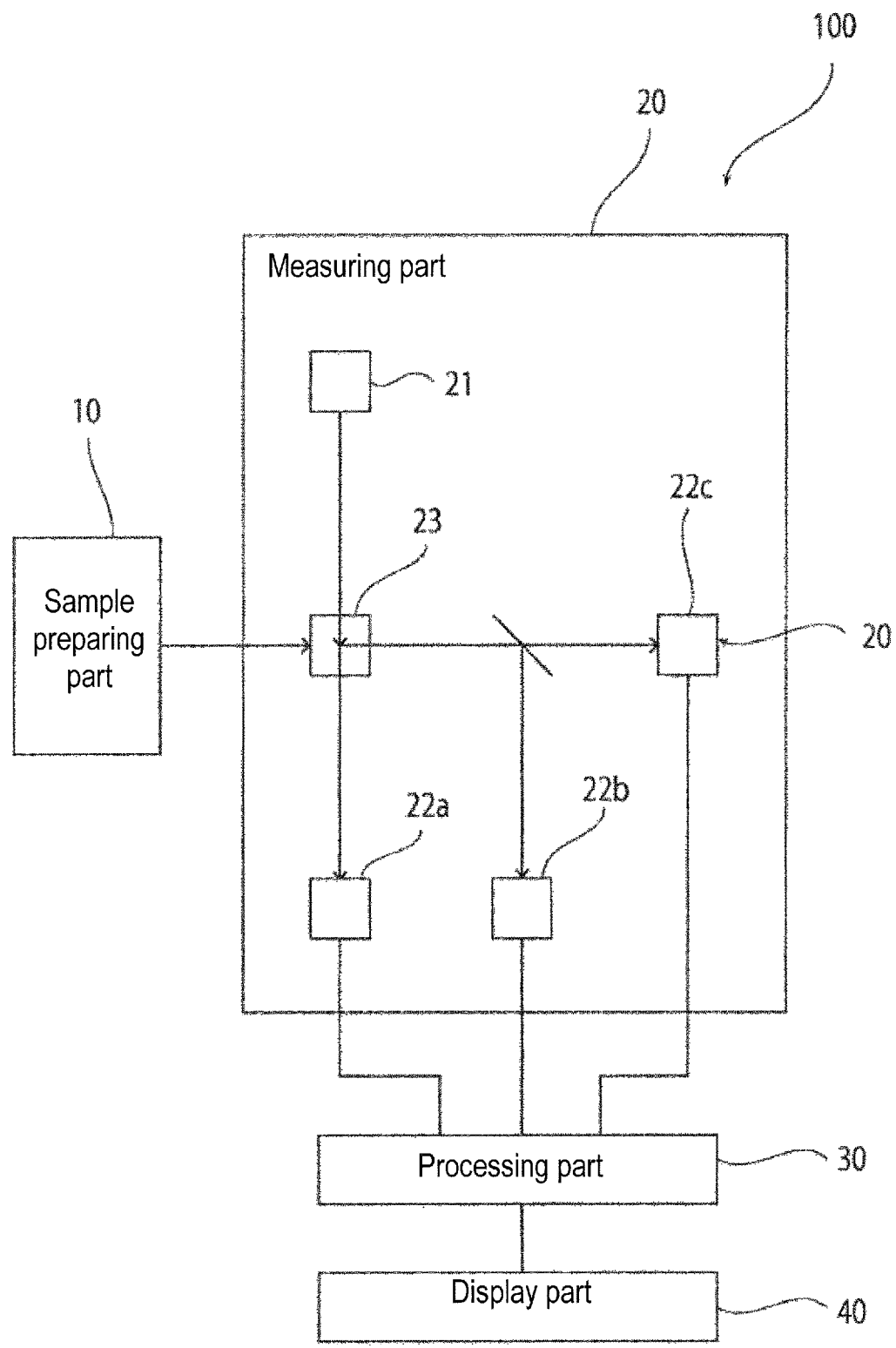
FIG. 1 is a brief block diagram of the blood analyzer of an embodiment of the invention.

FIG. 1 is a brief block diagram of the blood analyzer 100 of the embodiment. The blood analyzer 100 is a device for analyzing information related to various blood cells contained in blood using a flow cytometric method.

The blood analyzer 100 is provided with a sample preparing part 10. The sample preparing part 10 is the part that prepares measurement sample to be used in analysis. The sample preparing part 10 prepares a measurement sample by mixing a blood sample (whole blood), and various reagents such as hemolytic agent and fluorescent dye.

Hemolytic agent is a reagent for lysing red blood cells. Therefore, red blood cells are hemolyzed in the measurement sample containing hemolytic agent.

Hemolytic agent preferably contains, for example, a surfactant. Cationic surfactant is an example of a preferred surfactant. Cationic surfactant has strong lysing power. Cationic surfactant is used to hemolyze red blood cells, and to injure the cell membranes of normal white blood cells and abnormal mononuclear cells. Therefore, normal white blood cells and abnormal mononuclear cells are easily stained by fluorescent dye. Examples of preferred cationic surfactant include quaternary ammonium salt type surfactant and pyridinium salt type surfactant. Specific examples of preferred cationic surfactant are surfactants having 9 to 30 carbon total carbon atoms represented by, for example, structural formulae (I) and (II).

Formula (I)

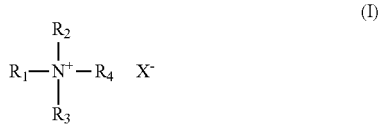

Formula (II)

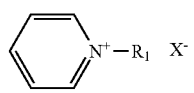

(In formulae (I) and (II), R1 is an alkyl group or alkenyl group having 6 to 18 carbon atoms. R2 and R3 are an alkyl or alkenyl group having 1 to 4 carbon atoms. R4 is an alkyl group having 1 to 4 carbon atoms, an alkenyl group or a benzyl group. X is a halogen atom.)

An alkyl group or alkenyl group having 6, 8, 10, 12, and 14 carbon atoms is preferable, while a straight-chain alkyl group is particularly preferred as R1. Specific examples preferred as R1 include octyl, decyl and dodecyl groups.

A methyl group, ethyl group and propyl group are particularly preferred as R2 and R3.

A methyl group, ethyl group and propyl group are preferred as R4.

Hemolytic agent, for example, may include surfactants other than cationic surfactant such as nonionic surfactants in addition to the cationic surfactant. Hemolytic agent also may include, for example, organic acids and buffer agents in addition to surfactant.

Fluorescent dye is an agent to stain nucleic acid. Red blood cells which do not have nucleic acid are therefore not stained by the fluorescent dye. Cells which have a nucleus such as nucleated red blood cells and white blood cells which have nucleic acid are stained by the fluorescent dye.

Examples of fluorescent dyes include propidium iodide, ethidium bromide, ethidium-acridine heterodimer, ethidium diazide, ethidium homodimer-1, ethidium homodimer-2, ethidium monoazide, trimethylene bis[[3-[[4-[[(3-methyl-benzothiazole-3-ium)-2-yl]methylene]-1,4-dihydro-quinoline]-1-yl]propyl]dimethyl aminium].tetraiodide (TOTO-1), 4-[(3-methyl-benzothiazole-2(3H)-ylidene) methylcarbamoyl]-1-[3-(trimethyl amino niobium)propyl]quinolinium-diiodide (TO-PRO-1), N,N,N',N'-tetramethyl-N,N'-bis[3-[4-[3-[(3-methyl-benzothiazole-3-ium)-2-yl]-2-propenylidene]-1,4-dihydro-quinolin-1-yl]propyl]-1,3-propanediaminium tetraiodide (TOTO-3), or 2-[3-[[1-[3-(trimethyl Ami niobium)propyl]-1,4-dihydro-quinoline]-4-ylidene]-1-propenyl]-3-methyl-benzothiazole-3-ium-diiodide (TO-PRO-3).

The measurement sample prepared in the sample preparing part is supplied to a measuring part 20. The measuring part 20 has the light source 21, the light receiving part 22, and a flow cell 23. The measurement sample is fed into the flow cell 23. A sheath fluid is fed together with the measurement sample to the flow cell 23. The measurement sample together with the sheath fluid flows through the flow cell 23.

The light source 21 irradiates light on the measurement sample within the flow cell 23. The light source 21 is configured by, for example, a semiconductor laser light source or the like. The wavelength of the might emitted by the light source 21 may be, for example, 633 nm.

Fluorescent light, side scattered light, and forward scattered light are produced when the light from the light source 21 irradiates the measurement sample. The forward scattered light is received by a forward scattered light receiver 22a. The forward scattered light receiver 22a outputs a forward scattered light signal which corresponds to the intensity of the forward scattered light to the processing part 30.

The processing part 30 is configured by a central processing unit (CPU) of a personal computer installed externally. Note that the processing part 30 is not limited to this configuration and also may be the central processing unit of a computer provided within the blood analyzer 100.

The side scattered light is received by a side scattered light receiver 22b. The side scattered light receiver 22b outputs a side scattered light signal which corresponds to the intensity of the side scattered light to the processing part 30.

The fluorescent light is received by a fluorescent light receiver 22c. The fluorescent light receiver 22c outputs a fluorescent light signal which corresponds to the intensity of the fluorescent light to the processing part 30.

The light receiving part 22 is configured by the forward scattered light receiver 22a, side scattered light receiver 22b, and fluorescent light receiver 22c. Note that the light receiving part 22 may be configured by, for example, photodiodes or the like.

The processing part 30 calculates information related to various blood cells and the like contained in blood as a measurement sample based on the input fluorescent light signal, side scattered light signal, and forward scattered light signal.

The processing part 30 detects the reactive B lymphocytes based on at least one of the fluorescent light signal and forward scattered light signal. The processing part 30 counts the reactive B lymphocytes based on the detection result. The processing part 30 outputs the number of reactive B lymphocytes as a count result.

More specifically, the processing part 30 discriminates white blood cells as reactive lymphocytes and white blood cells other than reactive lymphocytes based on the fluorescent light signals and side scattered light signals. The processing part 30 also discriminates the reactive B lymphocytes among the reactive lymphocytes based on at least one of the fluorescent light signals and forward scattered light signals. Note that the processing part 30 also may detect the reactive B lymphocytes among the lymphocytes after discriminating the white blood cells as lymphocytes and blood cells other than lymphocytes.

The processing part 30 also may discriminate white blood cells as reactive B lymphocytes, lymphocytes other than reactive B lymphocytes, and white blood cells other than lymphocytes based on the fluorescent light signals, side scattered light signals, and forward scattered light signals. White blood cells other than lymphocytes include, for example, monocytes, neutrophils, eosinophils, basophils and the like.

A display part 40 is connected to the processing part 30. The display part 40 shows the count results output from the processing part 30. The display part 40 at least shows the number of reactive B lymphocytes. The display part 40 shows, for example, at least one type of information selected from a group including the reactive B lymphocyte count, the reactive T lymphocyte count, the ratio of the reactive B lymphocyte count and reactive T lymphocyte count, the ratio of the lymphocyte count and the reactive lymphocyte count, and the ratio of the white blood cell count and the reactive lymphocyte count.

Blood Analyzing Method of the Blood Analyzer 100

The blood analyzing method of the blood analyzer 100 is described below.

Figure 2:
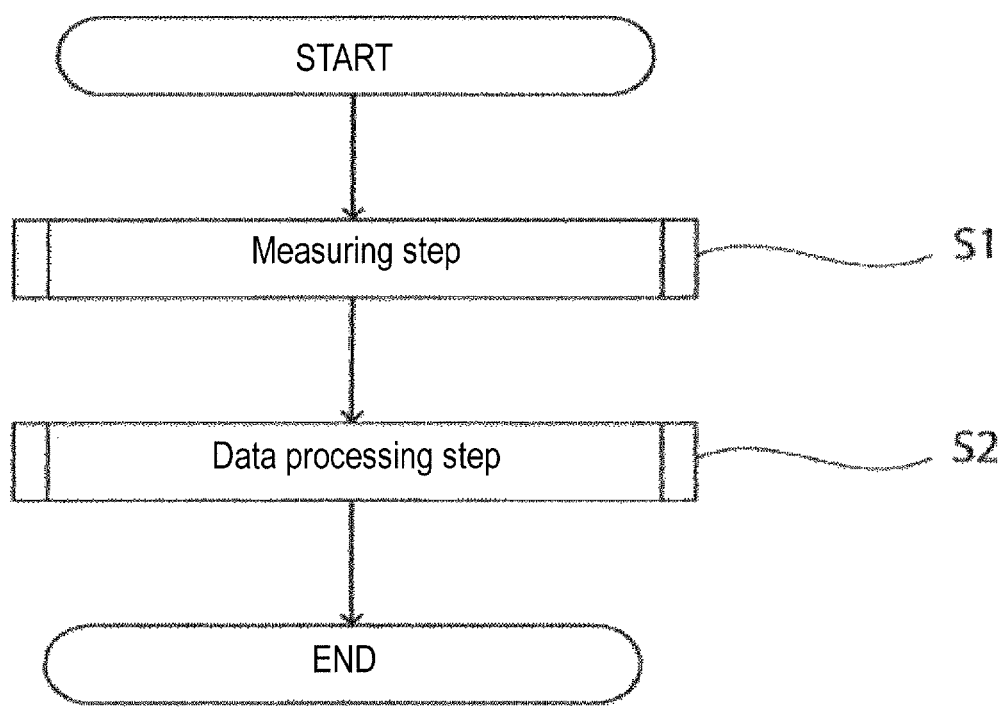
FIG. 2 is a flow chart of the blood analyzing method of an embodiment of the invention.

As shown in FIG. 2, the blood analyzing method of the blood analyzer 100 includes a measurement step S1 and a data processing step S2.

In the measurement step S1 of the blood analyzer 100, the sample preparing part 10 prepares a measurement sample by mixing a blood sample, a fluorescent dye for staining nucleic acid, and a hemolytic agent to hemolyze red blood cells. Specifically, a blood sample contained in a sample container is dispensed. The dispensed sample is then mixed with fluorescent dye and hemolytic agent in a mixing container to obtain a measurement sample.

The measurement sample is then irradiated by light from the light source 21. Specifically, the measurement sample is supplied together with the sheath fluid so as to flow through the flow cell 23. Light from the light source 21 is irradiated on the measurement sample flowing through the flow cell 23. When the light impinges the measurement sample, fluorescent light, side scattered light, and forward scattered light are produced. The forward scattered light receiver 22a receives the forward scattered light, and outputs forward scattered light signals corresponding to the intensity of the forward scattered light. The side scattered light receiver 22b receives the side scattered light, and outputs side scattered light signals corresponding to the intensity of the side scattered light. The fluorescent light receiver 22c receives the fluorescent light, and outputs fluorescent light signals corresponding to the intensity of the fluorescent light.

Then, in the data processing step S2, the processing part 30 counts the blood cells based on the obtained signals.

In the data processing step S2, at least the reactive B lymphocytes are detected based on at least one of the fluorescent light signals and forward scattered light signals. The reactive B lymphocytes are counted based on the detection results of the reactive B lymphocytes. At least the number of reactive B lymphocytes of the count result is output.

More specifically, in the data processing step S2, the white blood cells are discriminated as reactive lymphocytes and blood cells other than reactive lymphocytes based on the fluorescent light signals and side scattered light signals. The reactive B lymphocytes are also detected among the reactive lymphocytes based on at least one of the fluorescent light signals and forward scattered light signals in the data processing step S2.

In the data processing step S2, the reactive B lymphocytes also may be detected among the discriminated lymphocytes after discriminating the white blood cells as lymphocytes and blood cells other than lymphocytes. In the data processing step S2, white blood cells also may be discriminated at one time as reactive B lymphocytes, lymphocytes other than reactive B lymphocytes, and white blood cells other than lymphocytes based on the fluorescent light signals, side scattered light signals, and forward scattered light signals.

Figure 3:
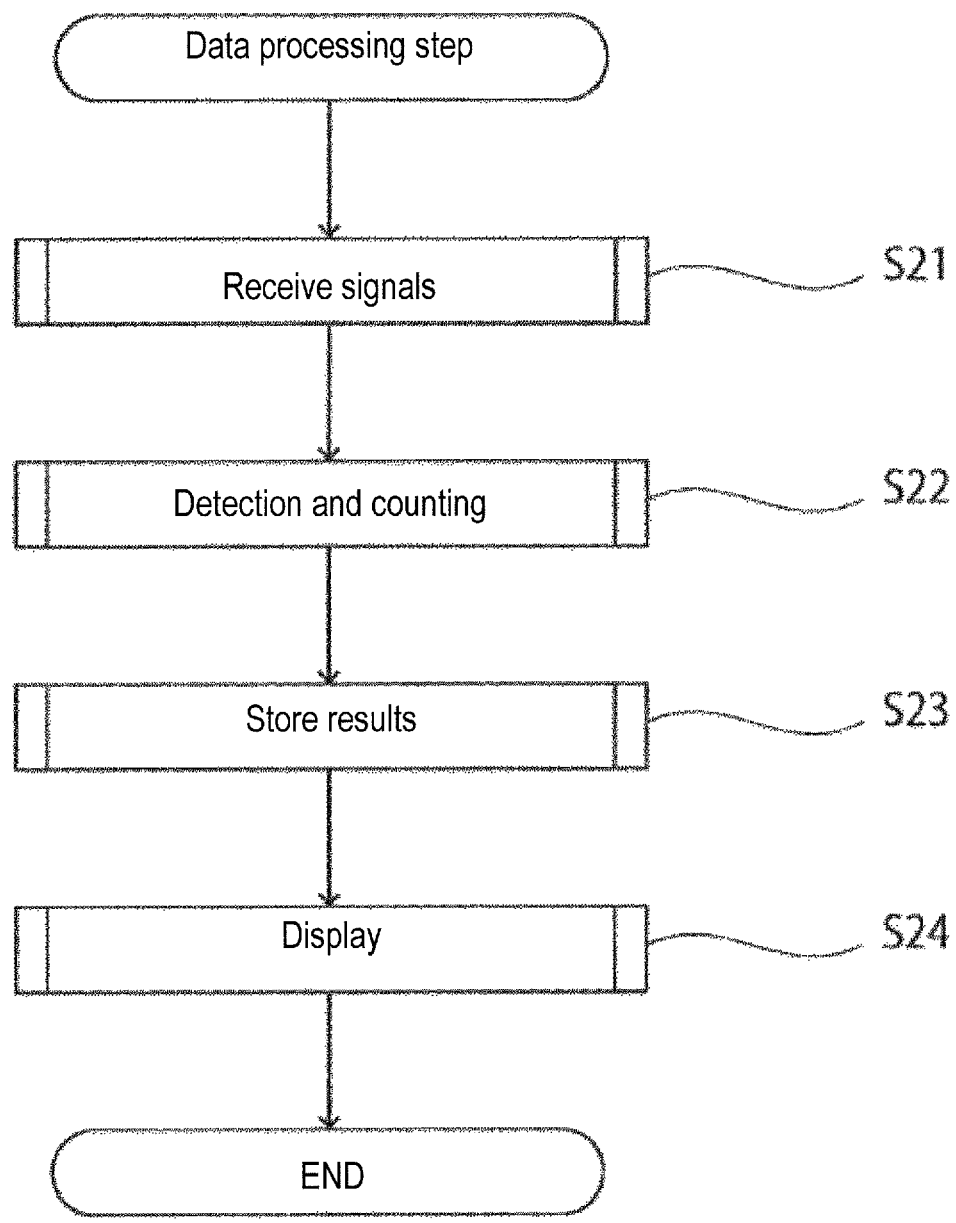
FIG. 3 is a flow chart of the data processing step of the blood analyzing method of an embodiment of the invention.

More specifically, the data processing step S2 may include, for example, a signal receiving step S21 in which the processing part 30 receives the fluorescent light signals, forward scattered light signals, and side scattered light signals from the receiving part 22, as shown in FIG. 3. The processing part 30 also may store the forward scattered light intensity, side scattered light intensity, and fluorescent light intensity corresponding to each particle in the obtained measurement sample as data associated with each particle in a memory.

In a detection and counting step S22, the processing part 30 next analyzes the data of the fluorescent light signals, forward scattered light signals, and side scattered light signals stored in memory, using an analysis program which is pre-stored in the memory.

Figure 8:
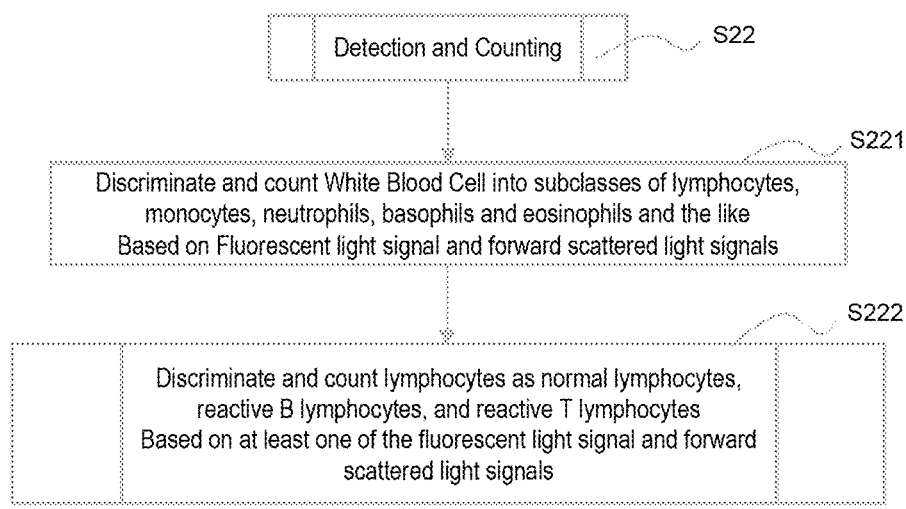
FIG. 8 is an expanded flow chart of the data processing step S22 in FIG. 3.

As shown in FIG. 8, the processing part 30 first discriminates the white blood cells in the measurement sample into subclasses of lymphocytes, monocytes, neutrophils, basophils, and eosinophils and the like based on the fluorescent light signals and side scattered light signals at step S221. Then, the discriminated lymphocytes are further discriminated as normal lymphocytes, reactive B lymphocytes, and reactive T lymphocytes, and respectively counted based on at least one of the fluorescent light signals and forward scattered light signals at step S222.

Then, in the results storing step S23, the processing part 30 stores the detection and count results obtained in the detection and counting step S22. In the display step S24, the processing part 30 displays the detection and counting results obtained in the detection and counting step S22 on the display part 40.

The present inventors, as a result of performing comparison experiments with clinical trials, have found that the measured fluorescent light intensity and the forward scattered light intensity are different in reactive B lymphocytes, reactive T lymphocytes, and in normal lymphocytes. Specifically, the fluorescent light signals and forward scattered light signals obtained from reactive T lymphocytes have stronger intensities than the fluorescent light signals and forward scattered light signals obtained from normal lymphocytes. The fluorescent light signals and forward scattered light signals obtained from reactive B lymphocytes also have stronger intensities than the fluorescent light signals and forward scattered light signals obtained from normal lymphocytes and reactive T lymphocytes. As a result, the present inventors conceived that reactive B lymphocytes and normal lymphocytes can be discriminated and the reactive B lymphocytes can be counted based on at least one of the fluorescent light intensity and forward scattered light intensity. Similarly, reactive T lymphocytes and normal lymphocytes can be discriminated and the reactive T lymphocytes can be counted based on at least one of the fluorescent light intensity and forward scattered light intensity.

From the perspective of greater accuracy in counting reactive B lymphocytes and reactive T lymphocytes, it is preferable that reactive B lymphocytes are counted based on the side scattered light intensity and at least one of the fluorescent light intensity and forward scattered light intensity. It is further preferable that reactive B lymphocytes are counted based on the side scattered light intensity, fluorescent light intensity, and forward scattered light intensity.

Reactive Lymphocyte Counting Method Examples

Examples of the method of counting reactive lymphocytes are described in more detail below.

Figure 4:
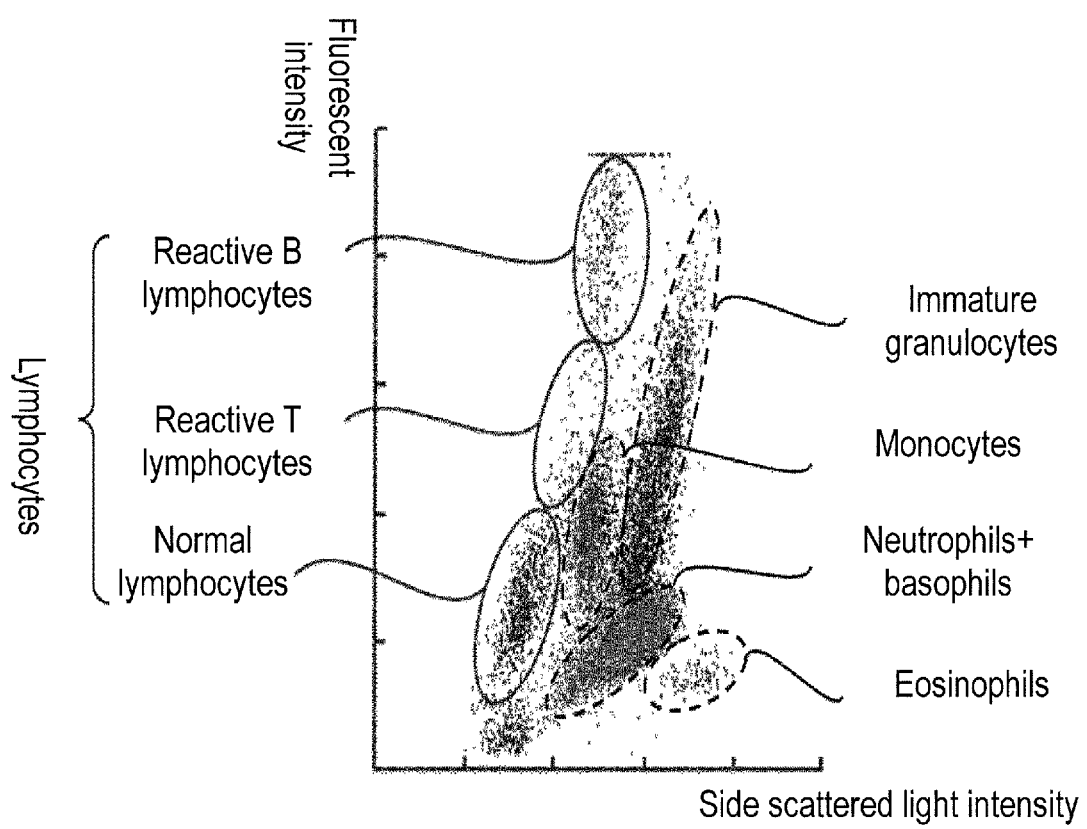
FIG. 4 is an example of a scattergram in which the axes are the side scattered light intensity and the fluorescent light intensity of a sample collected from a subject with an infectious disease.

A first example of the reactive lymphocyte detection and counting method is described using the scattergram of FIG. 4.

White blood cells in the measurement sample first are discriminated into subclasses of lymphocytes, monocytes, neutrophils, basophils, and eosinophils and the like based on the intensities of the fluorescent light signals and side scattered light signals.

In the first example, the discriminated lymphocytes are further discriminated as normal lymphocytes, reactive B lymphocytes, and reactive T lymphocytes based on the fluorescent light intensity and side scattered light intensity, which are the parameters used as the axes in constructing the scattergram shown in FIG. 4.

Each lymphocyte can be specifically discriminated by the specific method disclosed in Japanese Laid-Open Patent Application No. H5-149863 as a method for discriminating lymphocytes as normal lymphocytes, reactive B lymphocytes, and reactive T lymphocytes.

Figure 5:
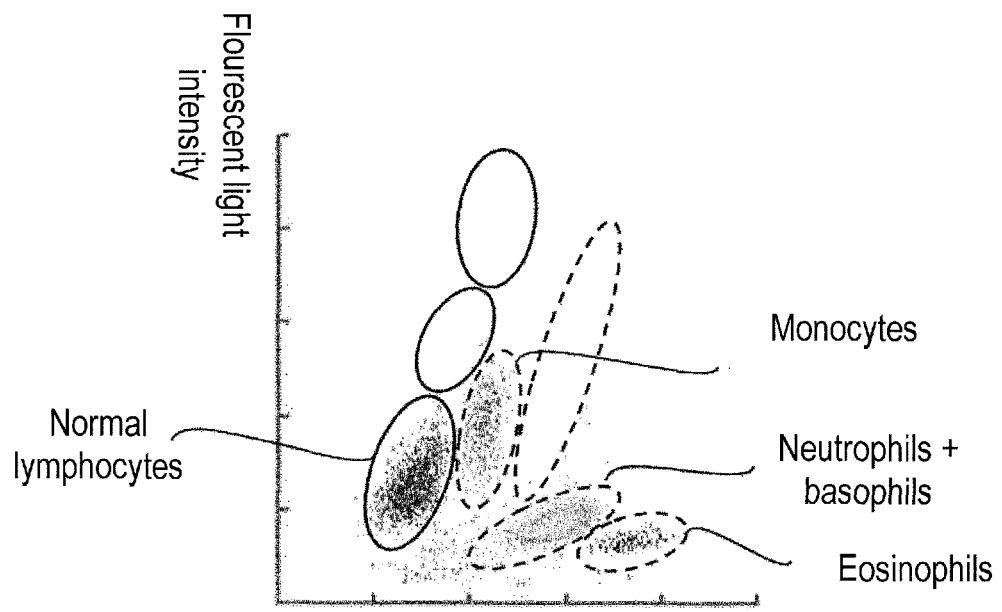
FIG. 5 is an example of a scattergram in which the axes are the side scattered light intensity and the fluorescent light intensity of a normal sample.

Specifically, fixed region first are set for the respective lymphocytes of normal lymphocytes, reactive B lymphocytes, and reactive T lymphocytes. The fixed region is set so that the degree of membership in a cluster becomes 1 relative to the fixed region of each lymphocyte within the fixed region. Next, the position of the initial center of gravity of the distribution is determined for each cluster based on the particle distribution within the cluster. Next, the position of the initial center of gravity is set as the center of gravity of each cluster, and the distance to the initial center of gravity is calculated for particles outside each fixed region. The degree of membership of each cluster is determined based on the calculated distance. Each particle is assigned to a cluster according to the degree of membership in the cluster, and the center of gravity position is redetermined for each cluster. Whether the difference between the previous center of gravity position and the current center of gravity position is less than a standard value is then determined. A new center of gravity position is determined until the difference between the previous center of gravity position and the current center of gravity position is less than the standard value, and the number of particles belonging to each particle cluster is calculated when the difference between the previous center of gravity position and the current center of gravity position becomes less than the standard value. The normal lymphocytes, reactive B lymphocytes, and reactive T lymphocytes can be specified by the above process. The number of reactive T lymphocytes and the number of reactive B lymphocytes can be combined to provide the total number of reactive lymphocytes.

a large number of lymphocytes appear in the region in which the fluorescent light intensity is high in the sample collected from a subject with an infectious disease shown in FIG. 4, whereas lymphocytes scarcely appear in the region in which the fluorescent light intensity is high in the normal sample shown in FIG. 5.

Figure 6:
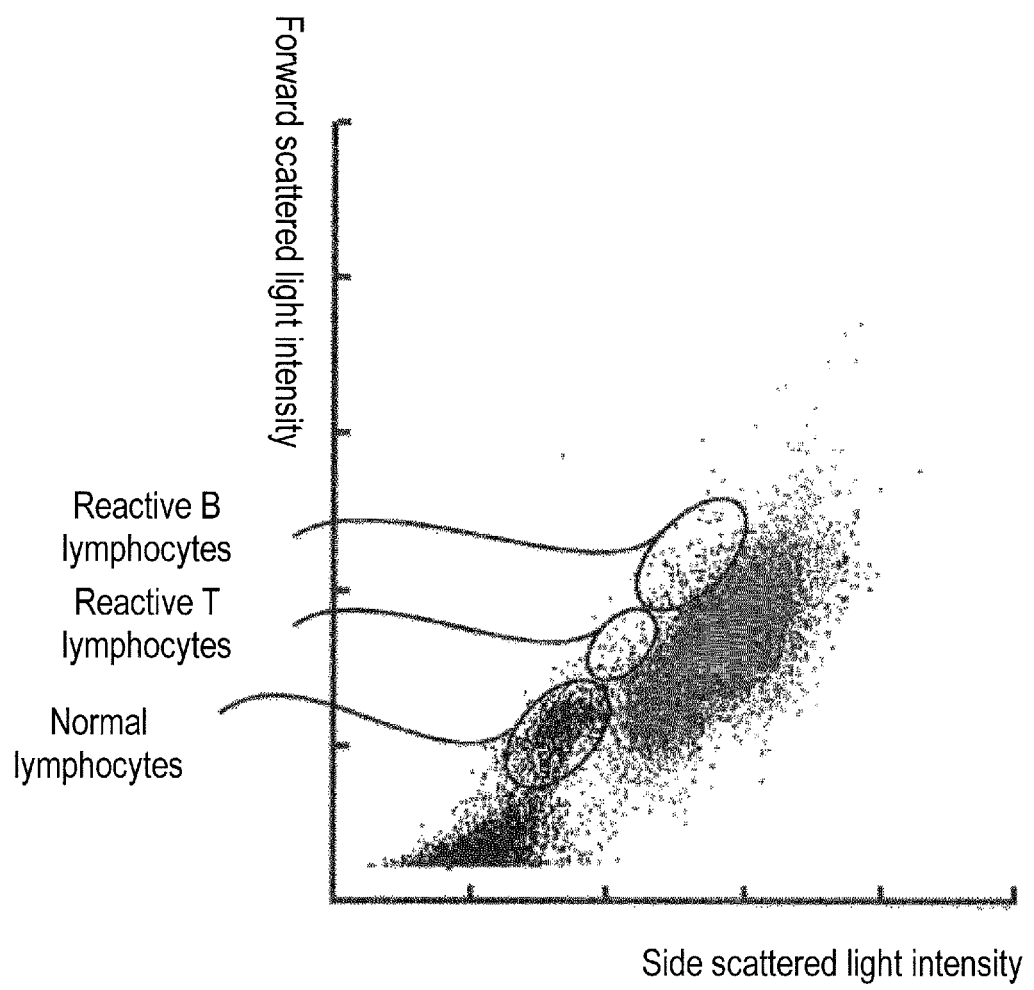
FIG. 6 is an example of a scattergram in which the axes are the side scattered light intensity and the forward scattered light intensity of a sample collected from a subject with an infectious disease.
Figure 7:
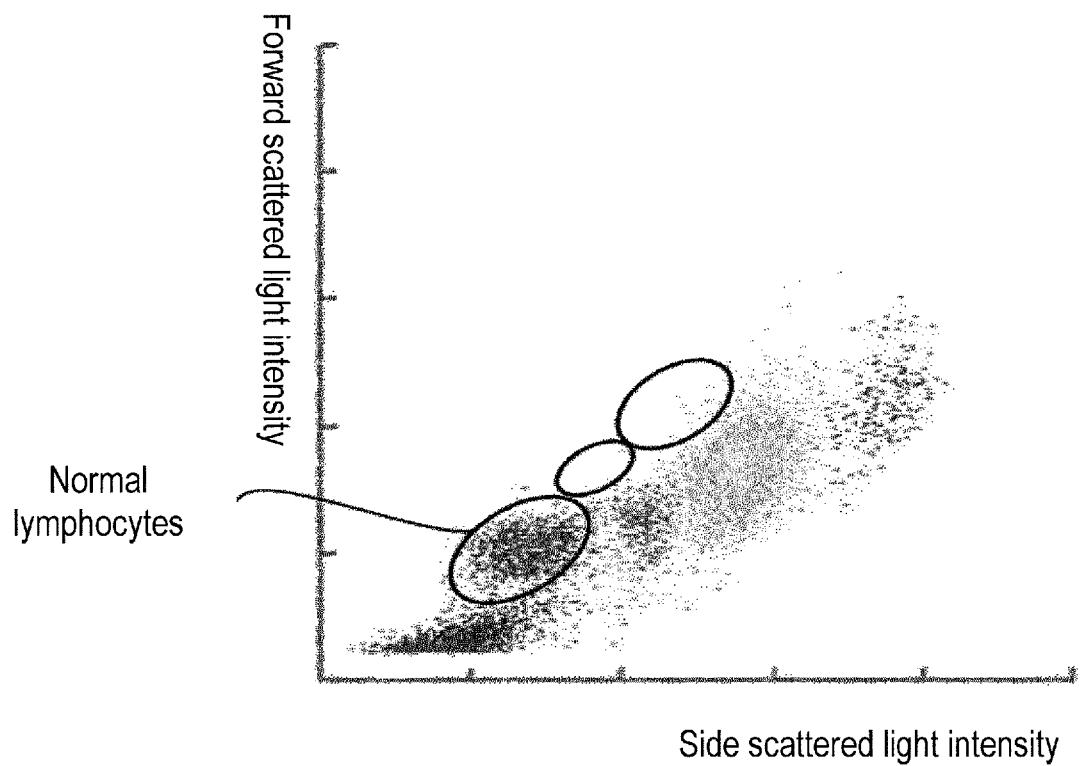
FIG. 7 is an example of a scattergram in which the axes are the side scattered light intensity and the forward scattered light intensity of a normal sample.

A method for specifying by the strength of the fluorescent light signal may also be used as a separate method of specifying each lymphocyte. Specifically, lymphocytes which have a fluorescent light intensity below a first threshold value are detected and counted as normal lymphocytes, lymphocytes which have a fluorescent light intensity between the first threshold value and a second threshold value that is higher than the first threshold value are detected and counted as reactive T lymphocytes, are detected and counted as normal lymphocytes, and lymphocytes which have a fluorescent light intensity above the second threshold value are detected and counted as reactive B lymphocytes, In the above example, each type of lymphocyte is detected using the fluorescent light intensity. However, the present invention is not limited to this example. For example, lymphocytes also may be discriminated based on the forward scattered light intensity as an axial parameter used to configure the scattergram shown in FIG. 6. Compared to the normal sample shown in FIG. 7, it is understood that lymphocytes appear in the region in which the forward scattered light intensity is high similar to the previously described fluorescent light intensity in the sample collected from a subject with an infectious disease shown in FIG. 6. As can be understood from FIGS. 4 and 6, discrimination using the fluorescent light intensity is preferable due to the higher resolution when discriminating lymphocytes as reactive B lymphocytes and reactive T lymphocytes.

As mentioned above, each type of lymphocyte may be detected using at least only fluorescent light intensity or only forward scattered light intensity when discriminating lymphocytes as reactive B lymphocytes and reactive T lymphocytes. Lymphocytes also may be discriminated based on fluorescent light intensity and side scattered light intensity, or forward scattered light intensity and side scattered light intensity rather than using only fluorescent light intensity and side scattered light intensity. Each type of lymphocyte also can be detected based on fluorescent light intensity, forward scattered light intensity, and side scattered light intensity.

Note that the present invention supplies a program for realizing the above described blood analyzing method to a computer or blood analyzer through a network or various types of storage media, and executes the program by the computer or blood analyzer reading the program.

EXPERIMENTAL EXAMPLES

Count results obtained using the blood analyzer 100 are described through experiments comparing with conventional methods.

The number of reactive T lymphocytes counted by the method of the present invention, and the number of CD8-positive T lymphocytes counted using fluorescently labeled CD8+ antibody were obtained from 48 samples provided by different subjects. A strong positive correlation was obtained when a correlation coefficient of 0.9336 was determined for the reactive T lymphocytes counted by the method of the present invention and the number of CD8-positive T lymphocytes counted using fluorescently labeled CD8+ antibody.

The proportion of the number of atypical lymphocytes relative to the number of lymphocytes was determined by observing cells using a microscope for the 48 samples obtained from different subjects mentioned above. A strong positive correlation was obtained when a correlation coefficient of 0.8968 was determined for the proportion of the number of reactive T lymphocytes relative to the number of lymphocytes counted by the method of the present invention and the proportion of the number of abnormal cells relative to the number of lymphocytes determined by the microscopic examination.

The number of reactive T lymphocytes counted by the method of the present invention is understood to be the number of abnormal cells, that is, T lymphocytes, and is strongly presumed to be the number of reactive T lymphocytes.

The proportion of the number of plasma cells relative to the number of lymphocytes was determined by observing cells using a microscope for 33 samples obtained from different subjects. A strong positive correlation was obtained when a correlation coefficient of 0.6108 was determined for the proportion of the number of reactive B lymphocytes relative to the number of lymphocytes counted by the method of the present invention and the proportion of the number of plasma cells relative to the number of lymphocytes determined by the microscopic examination.

From the above, the reactive B lymphocytes counted by the method of the present invention are strongly presumed to be plasma cells, that is, reactive B lymphocytes.

What is claimed is:

1. A blood analyzer comprising:
   a sample preparing part configured to prepare a measurement sample by mixing a blood sample including reactive B lymphocytes and other lymphocytes, a fluorescent dye for staining nucleic acid, and a hemolytic agent to hemolyze red blood cells;
   a light source configured to irradiate light on the measurement sample;
   a light receiving part configured to receive fluorescent light, forward scattered light, and side scattered light given off by the measurement sample irradiated by light, and output fluorescent light signals corresponding to the intensity of the fluorescent light, forward scattered light signals corresponding to the intensity of the forward scattered light, and side scattered light signals corresponding to the intensity of the side scattered light; and
   a central processing unit programmed to discriminate the reactive B lymphocytes from normal lymphocytes and reactive T lymphocytes based on at least one of the fluorescent light signals, forward scattered light signals, and a first threshold value stored in a memory accessible by the central processing unit, and to count the discriminated reactive B lymphocytes,
   wherein the intensity of the fluorescent light or forward scattered light signals from the reactive B lymphocytes is stronger than the intensity of the fluorescent light or forward scattered light signals of normal lymphocytes, and reactive T lymphocytes, and
   the central processing unit is programmed to count reactive B lymphocytes having fluorescent light or forward scattered light signals that are greater than the first threshold value.

2. The blood analyzer of claim 1, wherein the central processing unit is programmed to discriminate lymphocytes from blood cells in the measurement sample based on the fluorescent light signals and the side scattered light signals.

3. The blood analyzer of claim 1, wherein the central processing unit is programmed to discriminate and count the reactive B lymphocytes based on the side scattered light signals and the fluorescent light signals.

4. The blood analyzer of claim 1, further comprising:
   a display part configured to display the results output from the central processing unit, wherein the processing unit is configured to show the count results on the display part.

5. The blood analyzer of claim 4, wherein the display part is configured to show at least one type of information selected from a group including the reactive B lymphocyte count, a reactive T lymphocyte count, a reactive lymphocyte count, the ratio of the reactive B lymphocyte count and reactive T lymphocyte count, the ratio of the lymphocyte count and the reactive lymphocyte count, and the ratio of a white blood cell count and the reactive lymphocyte count.

6. The blood analyzer of claim 1, wherein the sample preparing part is further configured to prepare a measurement sample by mixing a blood sample including reactive T lymphocytes and other lymphocytes and,
   the central processing unit is further programmed to discriminate the reactive T lymphocytes from the normal lymphocytes and the reactive B lymphocytes based on at least one of the fluorescent light signals, forward scattered light signals, and the first threshold and a second threshold value, and
   wherein the intensity of the fluorescent or forward scattered light signals from the reactive T lymphocytes is weaker than the intensity of the fluorescent or forward scattered light signals of the reactive B lymphocytes and is stronger than the intensity of the light signals of the normal lymphocytes, and
   the central processing unit is programmed to count the reactive T lymphocytes having the fluorescent light or forward scattered light signals that are weaker than the first threshold value and greater than the second threshold value.

* * * * *